United States Patent [19]

Whitekettle et al.

[11] Patent Number: 5,468,739
[45] Date of Patent: Nov. 21, 1995

[54] METHODS FOR CONTROLLING ASIATIC CLAMS

[75] Inventors: Wilson K. Whitekettle, Jamison; Joseph C. Petrille, North Wales; Michael W. Werner, Warrington, all of Pa.

[73] Assignee: Betz Laboratories, Inc., Trevose, Pa.

[21] Appl. No.: 332,277

[22] Filed: Oct. 31, 1994

[51] Int. Cl.⁶ .............................. A01N 57/00; C02F 1/68
[52] U.S. Cl. ............................................. 514/75; 210/764
[58] Field of Search ................................. 514/75; 210/764

[56] References Cited

U.S. PATENT DOCUMENTS

| | | | |
|---|---|---|---|
| 2,906,595 | 9/1959 | Pelcak et al. | 21/2.7 |
| 3,142,615 | 7/1964 | Wehner | 167/22 |
| 4,188,380 | 2/1980 | Oswald | 514/75 |
| 4,328,638 | 5/1982 | Smithson | 43/124 |
| 4,462,914 | 7/1984 | Smith | 210/755 |
| 4,561,983 | 12/1985 | Davis et al. | 210/755 |
| 4,579,665 | 4/1986 | Davis et al. | 210/755 |
| 5,118,346 | 6/1992 | Wehner et al. | 106/18.3 |

FOREIGN PATENT DOCUMENTS 549006  11/1992  European Pat. Off. .

OTHER PUBLICATIONS

Mattice, J. S., 1979, "Interactions of *Corbiculat sp* with Power Plants", pp. 119–138, in J. C. Britton (ed), Processing, First International *Corbicula* Symposium, Texas Christian University Research Foundation, Ft. Worth, Texas.

Goss, L. B., 1979, "Control Studies on *Corbicula* for Steam–Electric Generating Plants", pp. 139–151, in J. C. Britton (ed.), Processing, First International *Corbicula* Symposium, Texas Christian University Research Foundation, Ft. Worth, Texas.

Smith, A. L., "Clams—A Growing Threat to Implant Water Systems", Plant Engineering, Jun., 1979, pp. 165–167.

29 CFR 176.300. Food and Drug Administration.

*Primary Examiner*—Allen J. Robinson
*Attorney, Agent, or Firm*—Alexander D. Ricci; Philip H. Von Neida

[57] ABSTRACT

Methods for controlling the fouling potential of Asiatic clams in aqueous systems are provided. The methods comprise adding to the aqueous system an effective controlling amount of a tetraalkyl phosphonium salt compound. The preferred compound is tri-butyltetradecyl phosphonium chloride.

4 Claims, No Drawings

# METHODS FOR CONTROLLING ASIATIC CLAMS

FIELD OF THE INVENTION

The present invention relates to control of fouling by Asiatic clams (Corbicula) in aqueous systems by utilizing a phosphonium based salt.

BACKGROUND OF THE INVENTION

Cooling systems for both industrial plants and utilities are subject to fouling by Asiatic clams whether the system is using cooling water on a once-through basis or of the recirculating type. The once-through systems operate by drawing cooling water through the process to be cooled on a one-time basis and discharge the water directly to the receiving body with a short residence time (usually minutes to hours) whereas recirculation cooling systems require the addition of only a fraction of the system volume as makeup water. Additionally, the service water systems (water, safety, and auxiliary cooling) which are often a part of these cooling systems are also quite vulnerable to macroinvertebrate fouling, primarily because they do not run continuously, and the conduits are of a smaller diameter.

The extent and type of Asiatic clam fouling will depend upon many factors such as the source of the cooling water, the season, the water temperature, the growth rate of the Asiatic clam, and the linear velocity of the cooling water. Because of the large quantities of cooling water used, the locality of the plant will dictate the water's source. A fresh water cooling system will be drawing from a river, lake or well, whereas plants situated along coastal areas will most likely utilize brackish or marine water for their cooling purposes.

Both once-through and recirculating types of cooling water are treated prior to entering the system by screening to remove objects which are large enough that they could damage pumps and heat exchange equipment. This screening does not prevent the passage of the early (microscopic) life-stages or larval stages of the Asiatic clams, which are the precursors to fouling as growth conditions are usually favorable within these systems. These early life stages of the Asiatic clams will settle out in low flow areas within the cooling system and grow and accumulate to a fouling size.

As a specific example of how Asiatic clams can cause fouling problems, a description of some characteristics are as follows:

One-year-old clams are capable of plugging valves and nozzles. Two-year-old clams can cause mechanical damage to impellers and other moving parts of water-distribution systems. At six years, the clam can damage tires of construction vehicles. As in all other clams, growth is rapid in early years and then tapers off. "Clams—A Growing Threat to Implant Water Systems", Plant Engineering, June, 1979, p. 165.

The Asiatic clams are very tolerant of many chemicals and often occur in great abundance. They have accumulated to depths of two meters in the Delta-Mendota Canal in California and have caused severe reduction in water flow. Some industrial plants have had difficulty obtaining fire insurance after inspectors found the fire protection systems plugged with Corbicula shells. Pump impellers have been damaged by shells in some industrial plants. The number of power plants which have experienced problems with Asiatic clams has been steadily increasing during the past several years. Problems in fossil-fueled power plants most often relate to pluggage of condenser tubes, surface water heat exchangers, and blockage of fire protection systems. In addition to these problems, nuclear power plants may have other problems associated with the shutdown service water and emergency reactor cooling systems. For further information, see also Mattice, J. S., 1979, "Interactions of *Corbicula sp* with Power Plants", pages 119–138 and Goss, L. B. et al., 1979, "Control Studies on Corbicula for Steam Electric Generating Plants", pages 139–151, in J. C. Britton (ed), Processing, First International Corbicula Symposium, Texas Christian University Research Foundation, Fort Worth, Tex., 313 pages.

Another threat to cooling water systems is *Dreissena spp*, the Zebra mussel, which has caused fouling problems in Europe and more recently, in North America. Morphologically, Asiatic clams are different from Zebra mussels. Asiatic clams in the larval stage are brooded in adult clam's gills and are not free swimming, while Zebra mussels in the larval stage are free swimming veligers. This allows Zebra mussel veligers to swim freely throughout any aqueous system they are present in and allows them to attach, by way of byssal threads, to any hard surface they come in contact with. As such, clustering of Zebra mussels can occur on these surfaces as they will even attach to other Zebra mussel shells. This formation of clusters will foul aqueous systems where they become situated.

Asiatic clams by their nature are burrowers which prefer silt and sand banks in which to live. Asiatic clams lack the ability to attach to substrates found in aqueous systems and fouling is generally the result of clogging of intake valves by the shells of the individual clams, whereas Zebra mussels will attach to all components in an aqueous system. This difference in morphology also dictates the type of treatment which is effective at controlling their growth. Given their spawning pattern and relatively non-mobile nature, Asiatic clams are effectively treated with a shock or one-time treatment of inhibitor chemicals. Zebra mussels are best treated by a continuous feed of chemicals over an extended period of time.

Fouling control of Asiatic clams has been attempted using physical/mechanical and chemical techniques (see, e.g., U.S. Pat. No. 4,328,638), but no foolproof combination has been developed. For example, chlorine, which has been by far the most used biofouling control agent, has several limitations: prolonged exposure times are required to achieve efficacy, chlorine demand of the cooling water reduces its potency, and strict environmental regulations are being imposed which act to severely limit the discharge of chlorine residues, and in some cases seek to eliminate its use altogether.

In addition to chlorine, Smith, U.S. Pat. No. 4,462,914 discloses the use of a high density cationic polymer to control Corbicula. While the polymer appears to be efficacious toward the adult clam after a six day exposure period, it suffers from some of the same drawbacks as chlorine.

The above-mentioned concerns over potential fouling biocides is well described by the following excerpt from the December 1983 Proceedings of the Electric Power Research Institute Symposium:

"Chemical controls have an inherent liability. What can kill inside the power plant may also impact the receiving water body: chemical toxicants are not specific. The perfect chemical would be stable enough to be effective inside the plant, but become nontoxic, via chemical reaction or decay, before or as it entered the receiving water body. So far, no chemical meets these specifications: chlorine and bisulfate/sulfide which have actually been used in an attempt to control Corbicula fouling have not been effective alone or have been successful only under limited conditions. Such a chemical may not exist, but scheduling of application of a chemical at the beginning of scheduled outages may offer a less stringent alternative, because of the possibility of extending holdup times."

U.S. Pat. No. 4,561,983 discloses the use of a nitrostyrene compound to control the fouling potential of Asiatic clams. U.S. Pat. No. 4,579,665 discloses the use of a nitrostyrene compound and an alkyl thiocyanate compound to control Asiatic clam fouling potential. Also, the compound of the present invention has been utilized for control of microorganisms, i.e., bacteria, fungi, and algae, but has not been suggested for control of larger, more complex organisms, especially macroinvertebrates, in aqueous systems. See, e.g., U.S. Pat. Nos. 2,906,595 and 3,142,615, and 21 CFR 176.300. Bacteria, fungi and algae microorganisms are dependent upon the presence of or absence of macroinvertebrates, such as mollusks, is essentially independent of the presence of metabolizable components in the water because they are much more complex organisms than microorganisms, both in terms of anatomic and physiological complexity and position in the food chain. Asiatic clams are unable to exist on metabolizable components. Rather, clams require microscopic bacteria and algae as foodstuff. Until the unexpected discovery of the applicants, the use of the compound of the present invention has never before been appreciated to control Asiatic clams.

U.S. Pat. No. 5,118,346 teaches the use of quaternary ammonium and phosphonium salts with fluoborate and fluophosphate anions formulated in paint to form antifouling paint films. These films are particularly effective at protecting objects immersed in seawater which are often covered with attached organisms such as mussels, barnacles and hydrozoans.

European patent application EP 0549 006 A2 teaches the use of ammonium and phosphonium salts including alkyl phosphonium chloride salts as biocides in general. Amongst the organisms which these salts are effective against are mussels. However, there is no teaching or discussion as to their effects against Asiatic clams. Further, these salts are taught to be used on or with solid or porous technical materials where they attack organisms such as mussels which attach to the solids.

DETAILED DESCRIPTION OF THE INVENTION

The present invention relates to methods for controlling the fouling potential of Asiatic clams in aqueous systems prone to such fouling comprising adding an effective inhibiting amount of a tetraalkyl phosphonium salt compound to said system.

The tetraalkyl phosphonium salt compound of the present invention has the formula:

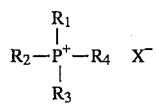

wherein $R_1$, $R_2$, and $R_3$ are alkyl groups containing about 1 to 16 carbon atoms, $R_4$ is an alkyl group containing about 1 to 24 carbon atoms, and X is an anion selected from the group consisting of chloride, bromide, iodide, sulfate, carbonate, phosphate, borate, and the like.

The preferred compound is tributyltetradecyl phosphonium chloride and is available from FMC Corporation under the tradename DP-350.

The Asiatic clams which are particularly affected by the tributyltetradecyl phosphonium chloride (TTPC) are more specifically Corbicula spp. The term "controlling" as used herein, is defined to cover eradication and inhibiting/preventing the growth of Asiatic clams in aqueous systems.

In accordance with the present invention, the TTPC treatment may be added to the desired aqueous system in need of Asiatic clam control, in an amount from about 50 ppb to about 20.0 ppm of the aqueous system to be treated. Preferably, about 0.125 ppm to about 2.0 ppm of TTPC is added to the aqueous system in need of Asiatic clam control. This low dosage for effective Asiatic clam control of 50 ppb proved surprising given dosages employed for other Asiatic clam control agents.

This invention may be used to control Asiatic clam fouling in cooling systems for both industrial plants and utilities which are subject to such fouling, whether the system is using cooling water on a once-through basis or is of the recirculating type. The present inventors anticipate that the present invention will control Asiatic clams in ballast water, cooling ponds and basins, intake structure areas, and ship reservoirs. The present invention may also be used to control all life stages of the Asiatic clams. For example, addition of TTPC in an effective amount to the incoming water of a once-through cooling system to eradicate small juveniles before they grow to large adult clams, provides adequate inhibition of clam infestation and the consequent build-up in the structure parts of the cooling water system. Furthermore, the destruction of adult clams could also be accomplished thereby eradicating fouling problems of a more mature nature.

The frequency and timing of the treatments would be by applying at different treatment intervals ranging from intermittent feedings to applications administered once a year to eradicate fouling organisms that have colonized or have grown within these systems. Treatment application strategies may include feeding the phosphonium salt compounds on a constant basis for a time sufficient to eradicate the fouling organism or treating the aqueous system by dosing the system statically. This would entail stopping water flow for a time and soaking the water for a time sufficient to control the Asiatic clam.

Known Asiatic clam control agents include oxidizing biocides such as chlorine, chlorine dioxide, bromine and ozone which can vary in treatment exposure from short, continuous exposures of one to four weeks to long exposures lasting several months. However, the use of oxidizing biocides to control Asiatic clams is significantly being restricted because of stricter environmental regulations. These regulations will severely limit discharge of chlorine residues, including the formation of carcinogenic trihalomethane compounds, and in some cases seek to eliminate them entirely.

The non-oxidizing, phosphonium based compounds of the present invention seek to avoid these difficulties associated with oxidizing biocides. The non-oxidizing, phosphonium based compounds are relatively inert to aqueous system metallurgy, more environmentally acceptable, and require significantly shorter exposure periods at surprisingly low concentrations.

The invention will now be further illustrated by the following examples which are included as being illustrative of the invention and which should not be construed as limiting the scope thereof.

EXAMPLES

Static bioassays were conducted with the TTPC formulation on Asiatic clams, *Corbicula sp*. Ten to twenty adult Asiatic clams were exposed to levels between 0.0078 and 20.0 mg/L (0.0078 to 20.0 ppm) as measured as 100% active ingredient. The bioassay was conducted at 20± 1° C. in 3.8 liter glass jars containing 3.0 liters of test solutions. Asiatic clams were exposed for 24 hours to test solutions. Following the 24-hour treatment exposure, test solutions were drained off and replaced with untreated laboratory-grade dilution water. Asiatic clam mortality responses were monitored daily during an observation period of up to seven days following the treatment. Cumulative percent mortality of Asiatic clams exposed to tributyltetradecyl phosphonium chloride are summarized in the following tables.

TABLE I

Test Series 1: Mortality response of Asiatic clams exposed for 24 hours to tributyltetradecyl phosphonium chloride follwed by a 6-day observation period.

| Active Concentration (mg/L) | Asiatic Clam Cumulative Percent Mortality (%) (n = 10 clams) |
|---|---|
| 0 (control) | 0 |
| 1.0 | 100 |
| 2.5 | 100 |
| 5.0 | 100 |
| 10.0 | 100 |
| 20.0 | 100 |

TABLE II

Test Series 2: Mortality response of Asiatic clams exposed for 24 hours to tributyltetradecyl phosphonium chloride follwed by a 7-day observation period.

| Active Concentration (mg/L) | Asiatic Clam Cumulative Percent Mortality (n = 20 clams) |
|---|---|
| 0 (control) | 0 |
| 0.125 | 100 |
| 0.25 | 95 |
| 0.50 | 95 |
| 1.00 | 100 |
| 2.00 | 100 |

TABLE III

Test Series 3: Mortality response of Asiatic clams exposed for 24 hours to tributyltetradecyl phosphonium chloride followed by a 11-day observation period.

| Active Concentration (mg/L) | Asiatic Clam Cumulative Percent Mortality (%) (n = 20 clams) |
|---|---|
| 0 (control) | 0 |

TABLE III-continued

Test Series 3: Mortality response of Asiatic clams exposed for 24 hours to tributyltetradecyl phosphonium chloride followed by a 11-day observation period.

| Active Concentration (mg/L) | Asiatic Clam Cumulative Percent Mortality (%) (n = 20 clams) |
|---|---|
| 0.0078 | 10 |
| 0.0156 | 40 |
| 0.0312 | 95 |
| 0.0625 | 90 |
| 0.1250 | 100 |

As seen in Tables I, II and III, cumulative mortality achieved 100% at dosages as low as 0.125 mg/L of tributyltetradecyl phosphonium chloride. A 95% cumulative mortality was achieved at levels as low as 0.031 mg/L. Thus, it can be seen that effective Asiatic clam control can be achieved in a range of about 0.031 to about 20.0 mg/L with a preferred low dosage range of 0.125 to about 2.00 mg/L.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what we claim is:

1. A method for controlling the fouling potential of Asiatic clams in an aqueous system of the type prone to such fouling and containing Asiatic clams comprising intermittently adding to said aqueous system an amount effective to control fouling of a tetraalkyl phosphonium salt compound having the formula

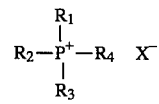

wherein $R_1$, $R_2$, and $R_3$ are alkyl groups containing about 1 to 16 carbon atoms, $R_4$ is an alkyl group containing about 1 to 24 carbon atoms, and X is an anion selected from the group consisting of chloride, bromide, iodide, sulfate, carbonate, phosphate, and borate.

2. The method as claimed in claim 1 wherein said tetraalkyl phosphonium salt compound is tributyltetradecyl phosphonium chloride.

3. The method as claimed in claim 1 wherein said tetraalkyl phosphonium salt compound is added to said aqueous system in an amount from about 50 parts per billion to about 20.0 parts per million parts of said aqueous system.

4. The method as claimed in claim 1 wherein said aqueous system is a cooling water system.

* * * * *